United States Patent [19]

Nemec

[11] Patent Number: 4,609,644
[45] Date of Patent: Sep. 2, 1986

[54] EPIPODOPHYLLOTOXINQUINONE GLUCOSIDE DERIVATIVES, METHOD OF PRODUCTION AND USE

[75] Inventor: Josef Nemec, Memphis, Tenn.

[73] Assignee: St. Jude Children's Research Hospital, Memphis, Tenn.

[21] Appl. No.: 620,844

[22] Filed: Jun. 15, 1984

[51] Int. Cl.$^4$ .................. A61K 31/70; C07H 15/26
[52] U.S. Cl. ........................... 514/27; 536/4.1; 536/18.1
[58] Field of Search .............. 536/18.1, 18.5; 424/180; 514/27

[56] References Cited

U.S. PATENT DOCUMENTS

| | | | |
|---|---|---|---|
| 3,408,441 | 10/1968 | von Wartburg et al. | 536/18.1 |
| 3,524,844 | 8/1970 | Keller-Juslen et al. | 536/18.1 |
| 3,592,808 | 7/1971 | Theander | 536/18.5 |
| 3,632,802 | 1/1972 | BeMiller et al. | 536/18.5 |
| 3,755,118 | 8/1973 | Partridge, Jr. | 536/18.1 |

OTHER PUBLICATIONS

Buchi et al., "Jour. of the American Chemical Society," 95, 2, Jan. 24, 1973.
Jardine, I., Anticancer Agents Based on Natural Product Models, 319-351 (1980).
Keller-Juslen, C., et al., Journal of Medicinal Chemistry, 14: 936-940 (1971).

Primary Examiner—Johnnie R. Brown
Attorney, Agent, or Firm—Saidman, Sterne, Kessler & Goldstein

[57] ABSTRACT

Novel compounds having the structural formula:

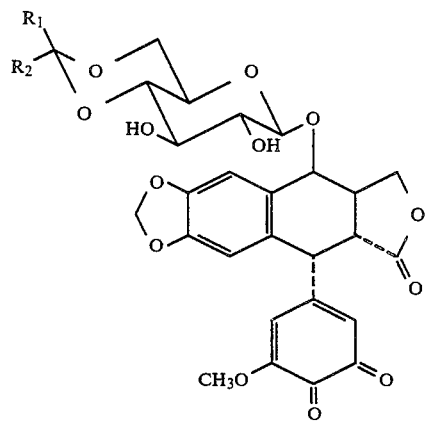

wherein $R_1$ is hydrogen and $R_2$ is alkyl, alkenyl, cycloalkyl, 2-furyl, 2-thienyl, aryl, aralkyl, aralkenyl, wherein the aromatic ring may be substituted by hydroxy, alkyl, alkoxy, halogen, amine, or nitro; or $R_1$ and $R_2$ are each and alkyl radical, or $R_1$ and $R_2$, together with the carbon atom to which they are attached, are a saturated cycloaliphatic ring, their methods of preparation, and the use of these new compounds as anti-cancer agents.

9 Claims, No Drawings

EPIPODOPHYLLOTOXINQUINONE GLUCOSIDE DERIVATIVES, METHOD OF PRODUCTION AND USE

BACKGROUND OF THE INVENTION

1. Field of the Invention

This invention is directed to new epipodophyllotoxin glucoside derivatives, to methods of preparing these new derivatives, and to the therapeutic use of these new derivatives. More particularly, this invention is directed to oxidized derivatives of epipodophyllotoxin glucosides having substantial water solubility. This substantial water solubility greatly increases the effectiveness of the new compounds both in ease of delivery and in elimination of the harmful clinical side effects associated with the solvent delivery systems employed with the precursor glycosides known to the prior art.

2. Description of the Background Art

Podophyllotoxin has the structural formula (I):

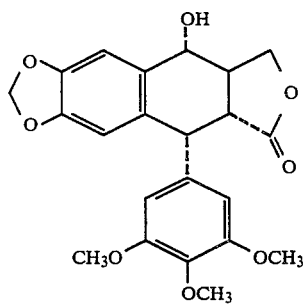

(I)

It is a naturally occurring compound which may be isolated from the roots and rhizomes of the American *Podophyllum peltatum L.* This compound, as well as some other structurally closely related lignans and lignan glycosides are known to exert a powerful and specific inhibition of mitosis. I. W. Kaplan, *New Orleans Med. Surg. J.*, 94:388 (1942); B. J. Sullivan and H. J. Wechsler, *Science*, 105:433 (1947); M. G. Kelly et al., *J. Nat. Cancer Inst.*, 14:967 (1954). However, clinical trials involving systemic application of these tumor-damaging agents have proven to be unsatisfactory due to non-specific toxicity of the various compounds.

Systematic chemical modification of the podophyllotoxin molecule has led to several therapeutically useful semi-synthetic preparations which are well absorbed enterally and possess a favorable ratio between antimitotic activity and non-specific toxicity. See Keller-Juslen, *Journal of Medicinal Chemistry*, (1971) Vol. 14, No. 10., pp. 936–940. Of particular interest are the 4'-demethylepipodophyllotoxin glucoside derivatives having the structural formula (II):

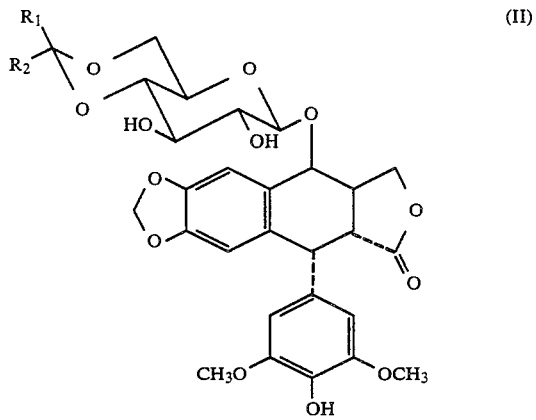

(II)

in which $R_1$ is hydrogen, and $R_2$ is an alkyl; alkenyl; cycloalkyl; 2-furyl; 2-thienyl; aryl; aralkyl; and aralkenyl, wherein the aromatic ring may optionally be substituted, preferably by one or more of hydroxy, alkyl, alkoxy, nitro, or halogen radicals. $R_1$ and $R_2$ may also each be an alkyl radical, or $R_1$ and $R_2$ together with the carbon atom to which they are attached, may form a saturated cycloaliphatic ring having five or six carbon atoms. These compounds, and the method for producing them, are disclosed in U.S. Pat. No. 3,408,441 to Wartburg et al. and U.S. Pat. No. 3,524,844 to Keller-Juslen et al. As disclosed in U.S. Pat. No. 3,524,844 to Keller-Juslen et al., compounds having the general formula (II) may be prepared by reacting 4'-demethylepipodophyllotoxin-beta-D-glucoside of the general formula (III):

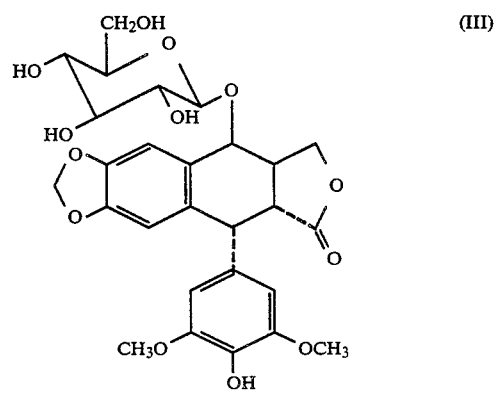

(III)

with a compound having the general formula (IV)

(IV)

where $R_1$ and $R_2$ are as described above. Alternatively the compound (III) may be reacted with a lower acetal or ketal thereof, in the presence of an acid, suitably a Lewis or sulphonic acid catalyst. The reaction is usually carried out in the absence of moisture and preferably carried out in the absence of oxygen, e.g., by providing a nitrogen atmosphere. Suitable Lewis acid catalysts include anhydrous zinc chloride. Suitable sulphonic acid catalysts include p-toluene sulphonic acid. Dimethylacetal, diethylacetal, the cyclic ethylene acetal or the corresponding ketals may be used as acetals or ketals of the compounds of formula (IV). It is preferred, in order to obtain a higher yield from the condensation, to remove the resulting reaction water or the resulting lower alcohol by azeotropic distillation in a vacuum at a low temperature or, in the case where water of reaction is formed, to use a catalyst which also has water-binding properties.

Among the compounds described above, two compounds corresponding to the general formula (II) are of particular interest and have been explored extensively. Etoposide corresponds to the general formula (II) wherein $R_1$ is hydrogen and $R_2$ is methy. Teniposide corresponds to the general formula (II) wherein $R_1$ is hydrogen and $R_2$ is 2-thienyl

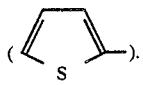

Research regarding these two compounds is described extensively by I. Jardine in "Anticancer Agents Based On Natural Product Models," Medicinal Chemistry, Vol. 16 (1980), pp. 319-351. As disclosed therein, both teniposide and etoposide have been found to be active in Ehrlich ascites tumor, sarcoma 37 and 180, Walker carcinosarcoma, mouse ependymoblastoma, and a variety of murine leukemias, as well as L-1210. Additionally, both compounds are effective in Hodgkin's disease and non-Hodgkin's lymphomas, especially reticulum-cell sarcoma. Teniposide shows definite anti-tumor activity in brain tumors and bladder cancer, while etoposide is active in acute nonlymphocytic leukemia, in small-cell lung cancer, and possibly in ovarian and thyroid cancer. However, in spite of the extreme importance as anti-cancer agents of these two compounds, the clinical usefulness of the drugs is significantly diminished by the fact that they are not, for practical purposes, water soluble. This lack of water solubility requires that they be formulated in a mixture of organic solvents, the solvents themselves exhibiting serious clinical side effects.

Thus a need has continued to exist for new, pharmacologically useful, epipodophyllotoxin glucoside derivatives having improved water solubility for use in anti-cancer therapy. The discovery of water soluble quinone derivatives makes possible clinical anti-tumor treatment which avoids the undesirable side effects which are a consequence of organic solvents employed previously in the administration of the prior art epipodophyllotoxin glucoside derivatives.

SUMMARY OF THE INVENTION

Podophyllotoxin was first discovered to have mitosis-inhibiting properties about 40 year ago. The non-specific toxicity of podophyllotoxin led to chemical modification of the molecule to produce glucoside derivatives having demonstrated therapeutic use against a variety of cancers. However, the glucoside derivatives, in spite of their anti-cancer effectiveness, have not proven to be completely satisfactory because the compounds are relatively insoluble in water, the compound not having sufficient solubility to permit administration as aqueous solutions. The organic solvents used to solubilize the prior art glucoside derivatives of epipodophyllotoxin for the preparation of injectable solutions create undesirable physiological side effects.

Accordingly, the present inventor, in an effort to circumvent the undesirable side effects of the solvents used to solubilize the prior art glucoside derivatives of epipodophyllotoxin, has invented new compounds which are derivatives of the prior art compounds and which are further characterized by being water soluble. The compounds of the present invention are a new class of compounds having the general formula (V):

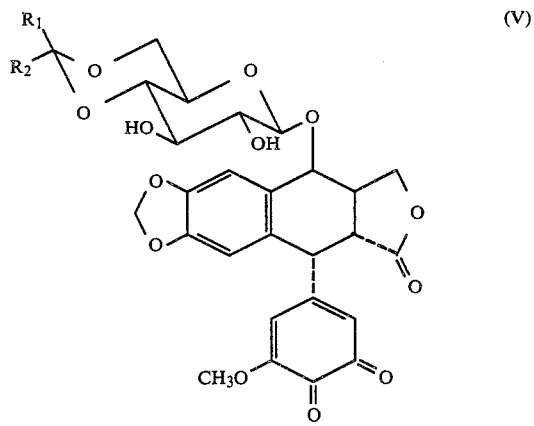

wherein $R_1$ is hydrogen, and $R_2$ is an alkyl; alkenyl; cycloalkyl; 2-furyl; 2-thienyl; aryl; aralkyl; and aralkenyl, wherein the aromatic ring may optionally be substituted, preferably by one or more of hydroxy, alkyl, alkoxy, nitro, or halogen radicals. $R_1$ and $R_2$ may be an alkyl radical, or $R_1$ and $R_2$, together with the carbon atom to which they are attached may form a saturated cycloaliphatic ring having five or six carbon atoms.

DESCRIPTION OF THE PREFERRED EMBODIMENTS

The epipodophyllotoxinquinone glucoside compounds of the present invention have the following structural formula (V):

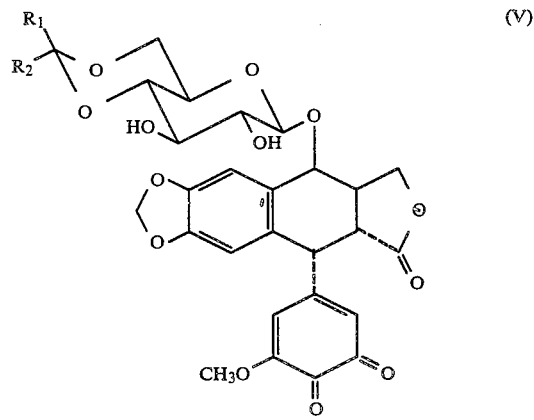

In the above formula, $R_1$ is a hydrogen atom and $R_2$ may be branched and straight-chain lower alkyls (i.e., having one to eight carbon atoms), branched and straight-chain alkenyls having two to eight carbon atoms; 5 to 6 membered cycloalkyl; 2-furyl; 2-thienyl; and aryl, aralkyl, or aralkenyl radical wherein the aromatic ring may be mono- or di-substituted by one or more groups comprising halide, lower alkyl, lower alkoxy, hydroxy, nitro, amine, phenylalkyl wherein the alkyl group contains one to four carbon atoms, and phenylalkenyl wherein the alkenyl group contains two to four carbon atoms. Additionally, $R_1$ and $R_2$ may be a lower alkyl radical or $R_1$ and $R_2$, together with the carbon atom to which they are attached, may be a saturated cycloaliphatic ring having five or six carbon atoms.

Preferred compounds are those compounds wherein $R_1$ is hydrogen and $R_2$ is methyl (etoposide derivative) or where $R_1$ is hydrogen and $R_2$ is

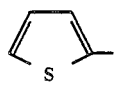

(teniposide derivative).

The compounds of the invention are synthesized by reacting an oxidizing agent with the appropriate 4'-demethylepipodophyllotoxin-beta-D-glucoside derivative. These derivatives have the general formula (II) above. The compounds and their methods of preparation, are described in U.S. Pat. No. 3,524,844 to Keller-Juslen et al.

Typical oxidizing agents include periodic acid and salts thereof, lead tetraacetate, oxygen, potassium nitrosodisulphonate, nitric acid, ferric chloride, and chromic acid, as well as anodic oxidation.

In general, 0.7–7.0 equivalents of oxidizing agent for each equivalent of glucoside derivative are employed. A preferred range of oxidizing agent is 1.0–6.0 equivalents, with 1.0–4.0 equivalents being the most preferred range.

The reaction may be carried out in a suspension or in an appropriate solvent or aqueous-solvent solution. The preferred solution is an aqueous dioxan solution.

Typical reaction temperatures are in the range of 0°–80° C., with 0°–50° C. being the preferred temperature range.

Suitable reaction times are in the range of one minute to eight hours.

On completion of the reaction, the desired product may be isolated from the reaction mixture by extraction with a suitable solvent, methylene chloride or chloroform being the preferred solvents. The product may be further purified by any suitable purification method, chromatography or crystallization being the preferred further methods of purification.

The compounds of the present invention demonstrate a surprisingly high solubility in water as compared to their corresponding precursor compounds. For example, etoposide has a solubility in water in the range of 0.1 to 0.2 mg/ml, while teniposide has a solubility in water in the range of 0.02 to 0.03 mg/ml. By comparison, the oxidized derivative of etoposide, that compound where $R_1$ is hydrogen and $R_2$ is methyl, has a solubility in water in the range of 3.8 to 5 mg/ml, while the derivative of teniposide, that compound wherein $R_1$ is hydrogen and $R_2$ is thienyl, has a solubility in water in the range of 0.2 to 0.4 mg/ml.

Additionally, the compounds and aqueous solutions of this invention may be prepared in combination with suitable pharmaceutical carriers.

The compounds of the present invention may be administered parenterally, i.e., subcutaneously, intravenously, intramuscularly, intraperitoneally, intrathecally or by transfusion.

The dosage administered will be dependent upon the age, health, and weight of the recipient, kind of concurrent treatment, if any, frequency of treatment, and the nature of the effect desired. Generally, daily dosage of active ingredient compound will be from about 0.05 to 1,000 mg/kg/wt. Preferred levels of administration of the active compound are in the range of about 0.1–200 mg/kg/wt, twice daily.

As mentioned above, typically the active compound is administered as an aqueous solution. However, it is within the contemplation of the present invention to administer the compound in other physiologically acceptable carriers as well. In such compositions, the active ingredient will ordinarily always be present in the amount of at least 0.03% by weight based on the total weight of the composition and not more than 90% by weight. Suitable physiologically acceptable carriers include saline, dextrose solution, N-methyl formamide, N,N-dimethyl formamide, polyethylene glycol, benzyl alcohol, ethyl alcohol, polyoxyethylene (20) sorbitan monooleate, and polyoxyethylated castor oil.

The epipodophyllotoxinquinone glucoside derivatives of the present invention have anti-cancer properties consonant with the prior art precursor compounds. As such, these compounds are effective against, among others, Ehrlich ascites tumor, sarcoma 37 and 180, Walker carcinosarcoma, ependymoplastoma, murine leukemias, L-1210, Hodgkins's disease, non-Hodgkin's lymphomas, brain tumors, bladder cancer, non-lymphocytic leukemia, small-cell lung cancer, ovarian cancer and thyroid cancer.

Having now generally described the invention, the same will be better understood by reference to certain specific examples, which are included herein for purposes of illustration only and are not intended to be further limiting.

EXAMPLE 1

Preparation of Etoposide
(4'-demethylepipodophyllotoxin-beta-D-ethylidene-glucoside)

1.5 g. of dry 4'-demethylepipodophyllotoxin-beta-D-glucoside was suspended in 30 ml. of nitromethane, and 6 ml. of acetaldehyde-dimethylacetal and 150 mg. of p-toluene-sulphonic acid was added. The mixture was stirred at room temperature in an atmosphere of nitrogen and in the absence of moisture for one hour. After this time, the initial suspension had turned into a clear solution, and no starting material could be detected in the thin layer chromatogram (silica gel plates, eluant: chloroform+6% of methanol). Working up was effected by diluting with 400 ml. of chloroform and shaking out three times with 25 ml. each of water. The crude material obtained after concentrating the dried organic phase by evaporation was subsequently chromatographed on 100 g. of silica gel "Merck" (grain size 0.05 to 0.2 mm.), whereby chloroform containing 6% of methanol was continuously used as eluant. 4'-demethylepipodophyllotoxin-beta-D-ethylidene-glucoside, which is uniform according to thin layer chromatography, was obtained. After recrystallization from methanol colorless crystals having a M.P. of 236°–251° C., $[\alpha]_D^{22} = -110.5°$ (c. =0.588 in chloroform), were obtained.

EXAMPLE 2

Preparation of Teniposide
(4'-demethylepipodophyllotoxin-beta-D-thenylidene-glucoside)

10 ml. of pure thiophene-2-aldehyde and 0.25 g. of anhydrous zinc chloride were added to 0.5 g. of dried 4'-demethylepipodophyllotoxin-beta-D-glucoside and the mixture was shaken on a machine at 20° C. in the absence of moisture, whereupon a clear solution was gradually obtained. The course of condensation was checked by thin layer chromatography, as described above. After a reaction period of three to four hours, the solution was diluted with chloroform and shaken out with water. The chloroform phase was washed twice more with a small amount of water and then dried over sodium sulphate and concentrated by evaporation. Excess thiophene-2-aldehyde was removed by dissolving the resulting residue in a small amount of acetone and reprecipitation was effected by adding pentane.

Reprecipitation from acetone/pentane was repeatedly effected until the condensation product results in flaky form. Further purification was effected in that the crude product was chromatographed on silica gel. The fractions which were uniform in accordance with thin layer chromatography were combined and yielded crystals from absolute alcohol. Pure 4'-demethylepipodophyllotoxin-beta-D-thenylidene-glucoside had a melting point of 242°–246° C. (last residue up to 225° C.) and had an optical rotation of $[\alpha]_D^{20} = -107°$ in chloroform/methanol (9:1).

EXAMPLE 3

Preparation of the Etoposide Derivative

To a magnetically stirred solution of etoposide (295 mg., 0.50 mmol.) in dioxane (5 ml.) and water (10 ml.) was added 0.5M aqueous solution of sodium metaperiodate (3.0 ml, 1.50 mmol.) in one portion. The reaction was carried out in the dark at 10±5° C. After 40 minutes, the reaction solution was saturated with ammonium sulfate and extracted with methylene chloride (5×10 ml). The combined extracts were washed with water (3×2 ml.), dried with magnesium sulfate and evaporated in vacuo to dryness to give the crude product (281 mg., 98.1%) as a red, amorphous powder. Recrystallization of this product from methylene chloride-ether, acetone-ether-hexane or methanol afforded an analytical sample, mp 241°–243° C. (dec.); TLC (silica gel), $R_f$ 0.32 (ether-acetone 3:1); NMR (CDCl$_3$) δ 1.39 (d, J=5 Hz, 3H, g-8), 2.56 (br, s, 1H, g$^2$-OH), 2.80 (br, s, 1H, g$^3$-OH), 2.7–3.8 (m, 7H, H-2, H-3, g$^2$-6ax), 3.85 (s, 3H, OCH$_3$), 4.13 (m, 1H, g-6eq), 4.23 (t, $J_{3,11}$=7 Hz, $J_{11,11''}$=9 Hz, 1H, H-11), 4.40 (d, $J_{11'',11}$=9 Hz, 1H, H-11''), 4.56 (d, J=6 Hz, 1H, H-1), 4.60 (d, J=9 Hz, 1H, g-1), 4.74 (d, J=5 Hz, 1H, g-7), 4.84 (d, J=3 Hz, 1H, H-4''), 5.15 (s, 1H, H-6'), 6.00 (s, 2H, OCH$_2$O), 6.45 (s, 1H, H-2'), 6.52 (s, 1H, H-8), 6.76 (s, 1H, H-5); IR (KBr) ν (cm$^{-1}$) 3460 (m, broad), 2900 (w, broad), 1770 (s), 1690 (w), 1660 (s), 1625 (m), 1560 (m), 1485 (s).

Analysis: Calculated for $C_{28}H_{28}O_{13}$: (572.5): C, 58.74; H, 4.93. Found: C, 58.56; H, 5.11.

EXAMPLE 4

Preparation of the Teniposide Derivative

A solution of teniposide (15.1 mg., 0.023 mmol.) in dioxane (0.50 ml.) and water (0.50 ml.) was treated with 0.5M aqueous solution of sodium metaperiodate (0.14 ml., 0.07 mmol.) in the dark at 15°±10° C. for 3 hours. The solution was saturated with ammonium sulphate and extracted with methylene chloride (4×1.5 ml.). The extracts were washed with water (3×0.3 ml.), dried with magnesium sulfate and evaporated in vacuo to dryness. The crude product was obtained as a red, amorphous solid (11.4 mg., 77.6%). Recrystallization of this product from acetone-ether-pentane or methylene chloride-ether-hexane afforded an analytical sample, mp 230°–233° C. (dec., turns yellow at 210° C.), TLC (silica gel) $R_f$ 0.45 (ether-acetone 3:1); IR (KBr) ν (cm$^{-1}$) 3460 (m, broad), 2900 (w, broad), 1770 (s), 1695 (w), 1665 (s), 1630 (m), 1560 (m), 1505 (m), 1485 (s).

Analysis: Calculated for $C_{31}H_{28}O_{13}S$ (640.5): C, 58.13; H, 4.41; S, 5.01. Found: C, 57.79; H, 4.54; S, 4.88.

EXAMPLE 5

The etoposide derivative of Example 3 was tested against murine leukemia L1210 in BDF$_1$ female mice with i.p. inoculum of 10$^6$ cells four times daily for seven days at 280 mg/kg/week. An increased lifespan (ILS) of 207% was observed and one animal of six was cured.

EXAMPLE 6

The etoposide derivative of Example 3 was tested against murine leukemia L1210 in BDF$_1$ female mice with i.p. inoculum of 10$^6$ cells at at 420 mg/kg/week, twice daily, for seven days. An ILS of 207% was observed and four of six treated BDF$_1$ female mice were cured.

Having now fully described the invention, it will be apparent to one with ordinary skill in the art that many changes and modifications can be made thereto without departing from the spirit and scope of the invention as set forth herein.

I claim as my invention:

1. A compound having the structural formula:

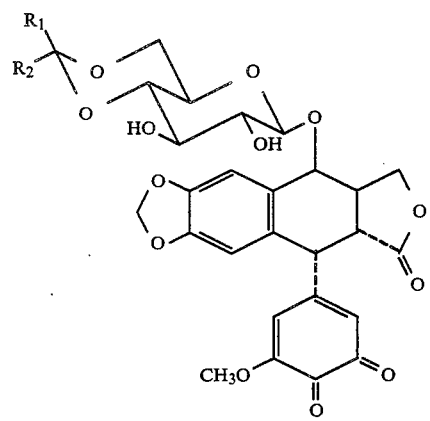

wherein R$_1$ is hydrogen and R$_2$ is selected from branched and straight-chain lower alkyls having one to eight carbon atoms; branched and straight-chain alkenyls having two to eight carbon atoms; 5 or 6 membered cycloalkyl; 2-furyl; 2-thienyl; aryl, aralkyl, or aralkenyl radical wherein the aromatic ring may be mono- or di-substituted by one or more groups comprising halide, lower alkyl, lower alkoxy, hydroxy, nitro, amine, phenylalkyl wherein the alkyl group contains one to four carbon atoms, and phenylalkyl wherein the alkenyl group contains two to four carbon atoms; or R$_1$ and R$_2$ are each an alkyl radical, or $R_1$ and $R_2$, together with the carbon atom to which they are attached, are a saturated cycloaliphatic ring having five or six carbon atoms.

2. The compound of claim 1 wherein $R_1$ is hydrogen and $R_2$ is selected from the group consisting of methyl and 2-thienyl.

3. The compound of claim 1 wherein $R_1$ is hydrogen and $R_2$ is methyl.

4. The compound of claim 1 wherein $R_1$ is hydrogen and $R_2$ is 2-thienyl.

5. A method for producing a compound having the structural formula:

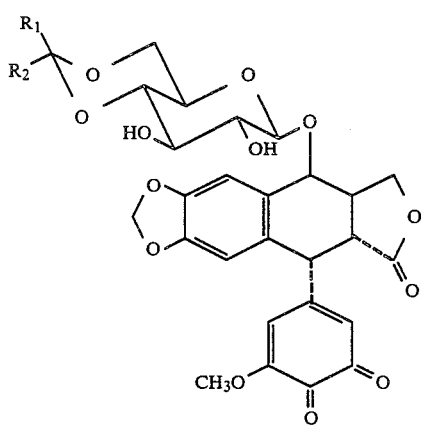

wherein $R_1$ and $R_2$ are as defined in claim 1, comprising reacting a compound having the structural formula:

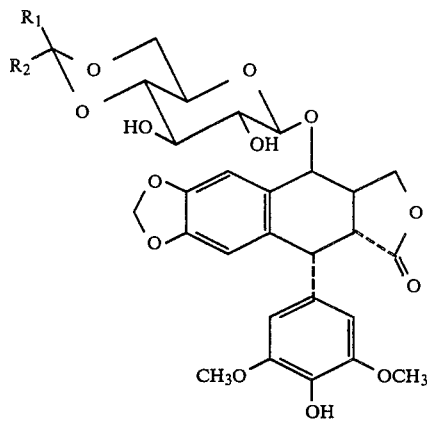

wherein $R_1$ and $R_2$ are as described above, with an oxidizing agent.

6. The method of claim 5 wherein the oxidizing agent is selected from the group consisting of periodic acid, salts of periodic acid, lead tetraacetate, oxygen, potassium nitrosodisulphonate, nitric acid, nitrous acid, ferric chloride, chromic acid, and anodic oxidation.

7. An anti-tumor composition comprising an effective amount of a compound according to claim 1 and a pharmaceutically acceptable carrier.

8. The anti-tumor composition of claim 7 wherein the pharmaceutically acceptable carrier is water.

9. A method for inhibiting the growth of cancer cells in an animal comprising administering to said animal an effective amount of a compound according to claim 1, wherein said cancer cells are selected from the group consisting of leukemia cells and sarcoma cells.

* * * * *